United States Patent [19]

Ramirez et al.

[11] Patent Number: 5,342,535

[45] Date of Patent: Aug. 30, 1994

[54] COMPOSITIONS CONTAINING KURROLL'S SALT

[75] Inventors: Jose E. Ramirez, Trumbull; Mohan Vishnupad, Monroe, both of Conn.

[73] Assignee: Imaginative Research Associates Inc., Bridgeport, Conn.

[21] Appl. No.: 51,568

[22] Filed: Apr. 21, 1993

Related U.S. Application Data

[63] Continuation of Ser. No. 748,042, Aug. 21, 1991, abandoned.

[51] Int. Cl.$^5$ ............................................... C11D 3/06
[52] U.S. Cl. ............................................. 252/135; 424/57; 424/601
[58] Field of Search ................... 252/135; 424/57, 601

[56] References Cited

U.S. PATENT DOCUMENTS

| | | | |
|---|---|---|---|
| 2,196,150 | 4/1940 | Heald et al. | 424/57 |
| 2,665,212 | 1/1954 | Roland | 99/25 |
| 2,852,392 | 9/1958 | Huber et al. | 99/108 |
| 2,870,093 | 1/1959 | Ruff | 252/137 |
| 3,000,831 | 9/1961 | Tuvell | 252/138 |
| 3,423,322 | 1/1969 | Cooper et al. | 252/135 |
| 3,814,797 | 6/1974 | Kasahara et al. | 424/128 |
| 4,021,360 | 5/1977 | McLaughlin et al. | 252/99 |
| 4,130,498 | 12/1978 | Lee et al. | 252/99 |
| 4,132,680 | 1/1979 | Nicol | 252/547 |
| 4,171,277 | 10/1979 | Dankworth et al. | 252/99 |
| 4,988,513 | 1/1991 | Griffity | 424/439 |
| 5,023,074 | 6/1991 | Morton et al. | 424/52 |

FOREIGN PATENT DOCUMENTS

| | | |
|---|---|---|
| 746448 | 5/1944 | Fed. Rep. of Germany . |
| 749139 | 11/1944 | Fed. Rep. of Germany . |
| 814145 | 9/1951 | Fed. Rep. of Germany . |
| 7222902 | 2/1973 | France . |
| 7809737 | 10/1978 | France . |
| 59-001409 | 1/1984 | Japan . |
| 1363388 | 8/1974 | United Kingdom . |
| 2233338 | 1/1991 | United Kingdom . |

OTHER PUBLICATIONS

Van Wazer, *Phosphorous And Its Compounds*, Interscience Publishers, Inc., N. Y., vol. I (1958) pp. 665–678.
Chem Abstract 611 b (1952) H. Ste,uml/u/ pel (Soap Factory, Hochdorf, Switzerland, *Textile-Praxis*, 7, 231–4 (1952).

*Primary Examiner*—Asok Pal
*Assistant Examiner*—P. Achutamurthy
*Attorney, Agent, or Firm*—Dilworth & Barrese

[57] ABSTRACT

Compositions containing potassium polymetaphosphate and a solubilizing agent are used to increase the viscosity of water and thereby improve the delivery and function of personal care, household and pharmaceutical products.

12 Claims, No Drawings

COMPOSITIONS CONTAINING KURROLL'S SALT

This is a continuation of copending application Ser. No. 07/748,042 filed on Aug. 21, 1991, now abandoned.

FIELD OF THE INVENTION

This invention relates to personal care, pharmaceutical and household product compositions, including soaps, that when mixed with water increase the viscosity of the water, improving the performance of the product. This invention also relates to processes for the production of the aforementioned products.

BACKGROUND OF THE INVENTION

Potassium polymetaphosphate, also known as potassium Kurrol's salt or potassium metaphosphate, is a polymeric metaphosphate of the formula $(KPO_3)_n$, where n is the degree of condensation and is usually much greater than 100. The Kurrol salts are generally made by dehydrating monopotassium orthophosphate, resulting in a straight chain polyphosphate with a high degree of polymerization. The degree of polymerization can range from several hundred to several million phosphorous atoms per chain, depending upon the conditions under which the chemical reaction is carried out.

A survey of the chemistry of potassium polymetaphosphate is provided by J. R. Van Wazer in *Phosphorous And Its Compounds*, Interscience Publishers, Inc., New York, a division of John Wiley and Sons, Inc., Vol. I, (1958), pages 665–678, which is incorporated herein by reference.

Potassium polymetaphosphate has been used in the food industry as an emulsifier and as a moisture retaining agent, particularly in connection with ground meat products (See U.S. Pat. No. 2,852,392).

U.S. Pat. No. 2,655,212 discloses aqueous solutions or dispersions of potassium Kurrol salt and one or more solubilizing agents which are reacted with aqueous dispersions containing milk protein. Added to milk, the resulting polymer/milk protein gels are disclosed to be useful as thickening or stabilizing agents, particularly in chocolate milk drinks.

Potassium polymetaphosphate has also been evaluated for use as a builder for laundry detergent products. H. Stüpel (Soap Factory, Hochdorf, Switzerland, Textile-Prayis 7,231-4) (1952). The detergenty of various soap and phosphate-builder combinations containing high levels of phosphates (0.5 g–6.0 grams of phosphate-builder with 1–2 grams of soap) were tested.

Potassium polymetaphosphate has a very low solubility in water but good solubility in dilute solutions of salts with singly charged cations other than potassium.

The dissolution of potassium polymetaphosphate in a solution containing monovalent cations other than potassium occurs via an ion exchange process. Singly charged cations replace the potassium ion in the dispersed, long chained, linear molecules of $(KPO_3)_n$. An excess of the singly charged cations causes the formation of a gelatinous mass which upon dilution gives a viscous solution. The ion-exchange reaction which occurs in the aqueous media thus results in the solubilization of the complex phosphate compound and produces clear gels. The gels are not stable since significant hydrolysis of the polymer occurs over relatively short times (typically under two hours) resulting in a substantial loss of viscosity.

SUMMARY OF THE INVENTION

In accordance with the present invention, unique applications have been discovered for novel compositions comprising mixtures of potassium polymetaphosphate and a solubilizing agent, preferably salts of sodium and/or lithium, the mixture containing substantially no water or only small amounts of residual moisture. In accordance with a further aspect of this invention, the compositions of this invention are incorporated into personal care, pharmaceutical and household products. The ingredients of the different products are blended in the absence of water with the mixture of potassium polymetaphosphate and solubilizing agent. The resulting products when combined with water will show marked viscosity increases in the water which are easily perceived by the user of the end application.

In yet other aspects, the present invention encompasses processes for the preparation and/or use of the personal care, household or pharmaceutical products.

DETAILED DESCRIPTION OF PREFERRED EMBODIMENTS

The compositions of the present invention comprise a mixture of potassium polymetaphosphate and a solubilizing agent which mixture is substantially free from water. Potassium polymetaphosphate may be synthesized using known techniques and is commercially available as a high molecular weight potassium phosphate polymer from Gallard-Schlesinger Industries, Inc.

Solubilizing agents useful in this invention include any source of monovalent cations which readily substitute for potassium in the polymer. Particularly useful are inorganic and organic salts of sodium and lithium, such as, for example sodium halides, sodium bicarbonate, sodium phosphate, sodium sulfate, sodium citrate, sodium lauryl sulfate, sodium cocoyl isethionate, sodium tallowate, sodium cocoate, chlorinated trisodium phosphate, lithium halides, lithium sulfate, lithium hypochlorite, lithium tallowate, and lithium cocoate. The salt forms of detergents, surfactants or fatty acids may be the source of monovalent cations. For example, sodium ions may be supplied by sodium cocoate, sodium tallowate, or the like, that although by themselves show limited solubility, they provide sufficient quantities of sodium ion to solubilize the Kurrol phosphate for functional purposes.

The particular solubilizing agent chosen will depend in large part upon the particular application for the composition. For example, where the application involves contact with the skin or ingestion by the user, a solubilizing agent should be chosen which will not impart toxicity, foul taste or offensive smell to the product. As another example, where an effervescent product is desired, sodium bicarbonate may appropriately be chosen as the solubilizing agent.

The compositions of the present invention will preferably include substantially equal amounts by weight of potassium polymetaphosphate and solubilizing agent or an excess of solubilizing agent. Additionally, the compositions of this invention contain substantially no water or only small amounts of residual moisture. By substantially no water it is meant that the compositions usually include less than five percent by weight of water. Preferably, the compositions of the invention contain less than 0.1 percent by weight of water. Most preferably, the compositions of this invention include no added water, but only include the water of hydration of the various ingredients.

An exception will be the case where the product is formed into a solid form such as, for example non-effervescent tablets or soap and synthetic detergent bars. In such cases, water may be added during processing of the product and then removed upon drying of the solid form (for example by evaporation) so that the finished product is substantially free from water.

In one aspect, the compositions of the present invention are formulated as personal care products. By the term "personal care products" it is meant that the product is formulated to include functional ingredients for an application wherein the product will be placed into contact with the person of the user. Personal care products include, but are not limited to, cosmetics, cleansers for the skin, hair or other parts of the body, bath gels, deodorants, soap and synthetic detergent bars, and body powders. The term "personal care products" is also intended to include products formulated for the care of prosthetic devices such as, for example, denture cleansers.

In another aspect, the compositions of the present invention are formulated as household products. By the term "household products" it is meant that the product is formulated to include functional ingredients for an application wherein the product will be placed into contact with the surface of articles. Normally, a household product will include ingredients which are irritants to the skin, eyes or olfactory and thus are inappropriate as personal care products. Household products include, but are not limited to, toilet bowl cleaners, basin, tub and tile cleaners, glass cleaners, abrasive-type cleansers, floor cleaners, car cleaners.

In yet another aspect, this invention embraces pharmaceutical products. By the term "pharmaceutical products" it is meant that the product is formulated to include active ingredients which provide some therapeutic response or effect by contact with or ingestion by the user. Pharmaceutical products include, but are not limited to medicated syrups, analgesic soaks, medicated cleansers or the like and mouth rinses or mouthwashes.

For each category of product, suitable functional or active ingredients are added to the composition to provide the desired function or effect for the product. For example, for personal care products suitable functional ingredients include sodium salts of soaps and detergents, $NaHCO_3$ and NaCl. As further examples, for household products suitable functional ingredients include sodium detergents, bleaching agents and $NaHSO_4$. As additional examples, for pharmaceutical products suitable active ingredients include any therapeutic agent such as fluoride, analgesics, antihistamines and antitussives. In preferred compositions, the functional or active ingredient may also constitute the solubilizing agent, thereby reducing the number of ingredients in the composition resulting in a corresponding reduction in the cost of preparing the composition.

Other optional ingredients may also be present, including fragrance, coloring, flavoring, preservatives, tableting materials and the like.

When formulated as household, personal care or pharmaceutical products, the compositions of this invention are prepared having substantially no water and are added to water only immediately prior to use, that is, within about one hour of use.

Typical properties of water when mixed with compositions in accordance with the present invention are shown in Table I.

TABLE I

| Composition* $(KPO_3)_n$ | | Water | Viscosity** | Comments*** |
|---|---|---|---|---|
| | Na CL | | | |
| — | — | 100 | 1 | a |
| 0.5 | 0.5 | 99 | 18 | b |
| 0.5 | 1.0 | 98.5 | 40 | b |
| 0.5 | 2.0 | 97.5 | 13 | b |
| — | 1 | 99 | 1 | a |
| 0.5 | — | 99.5 | 1 | a |
| | $NaHCO_3$ | | | |
| 0.5 | 1.0 | 98.5 | 21 | b |
| 0.5 | 2.0 | 97.5 | 21 | b |
| | $Na_2SO_4$ | | | |
| 0.5 | 1.0 | 98.5 | 36 | b |
| 0.5 | 2.0 | 97.5 | 19 | b |
| | LiCl | | | |
| 0.5 | 0.5 | 99.0 | 175 | b |
| — | 0.5 | 99.5 | 1 | a |

*Parts by weight.
**Of freshly prepared solutions; in centipoise at 20° C.
***Key to Comments:
a = Water-like viscosity, no significant after-feel upon drying.
b = Viscous liquid, excellent skin feel after drying.

The invention is further exemplified by the following listed applications, but not limited to the examples contained therein.

A unique application of potassium metaphosphate and a solubilizing agent is in the preparation of bath salts. For this purpose potassium Kurrol salt and a solubilizing agent, preferably sodium chloride, sodium citrate, sodium bicarbonate, sodium phosphate or sodium sulphate, are used.

From a user perception, the bath salt composition that is preferred results when you add 40g of the following composition to 100 liters of bath water.

EXAMPLE 1

Bath Salt

| Ingredient | % by weight |
|---|---|
| $(KPO_3)_n$ | 30.0 |
| NaCl | 67.0 |
| Mineral Oil | 2.3 |
| PEG-8 Dilaurate | 0.2 |
| Fragrance | 0.5 |
| | 100.00 |

The concentration of salt in bath water is 120 ppm $(KPO_3)_n$ and 268 ppm NaCl. The viscosity of the bath water is approximately 2–3 cps, however it could vary somewhat depending on concentration gradients in the tub as the potassium polymetaphosphate is first dispensed and solubilized. Such a concentration gives a lotion-like perception to the bath water and is easily rinsable after immersion in the tub. The lotion-like bath gives an effect which is perceived by the user of leaving the skin soft and conditioned.

Example 2 illustrates the composition of a tablet which will effervesce to increase ease of disintegration of the tablet and to provide faster, more homogenous dissolution. The effervescent tablet dosage form provides the optimum form of addition of this particular type of product (i.e., bath salt) to water, since it minimizes the formation of concentration gradients that could cause the user to slip and fall in the tub.

EXAMPLE 2

Effervescent Bath Tablet

| Ingredient | % by weight |
| --- | --- |
| $(KPO_3)_n$ | 20.00 |
| $NaHCO_3$ | 36.99 |
| Citric Acid | 37.15 |
| Mineral Oil | 3.00 |
| PEG-8 Dilaurate | 2.00 |
| Fragrance | .50 |
| Blue #1 | .03 |
| Fumed Silica | .33 |
| | 100.00 |

A 40 g tablet prepared with the composition listed on Example 2 is to be added to 100 liters of bath water with results similar to those described in Example 1.

Another unique application of potassium polymetaphosphate and a solubilizing agent is in the formulation of a toilet bowl cleaner. It is quite desirable to thicken the toilet bowl water immediately as you add the dry dosage form to the toilet bowl. The thickened, gel-like toilet bowl water containing detergents, acid or bleaches and other ingredients will clean the bowl reducing the splashing, while clinging to the underside of the rim and other difficult to reach areas. A preferred toilet bowl cleaning composition is exemplified in Example 3.

EXAMPLE 3

Toilet Bowl Cleaner

| Sodium Lauryl Sulfate | 5.0 |
| --- | --- |
| $(KPO_3)_n$ | 30.0 |
| NaCl | 62.0 |
| LiOCl | 3.0 |
| FD&C Blue #1 | as needed |
| Fragrance | as needed |

A 20 g tablet of the above composition will be added to the toilet bowl. Upon dissolution the resulting viscous liquid is readily brushed around the toilet bowl for quick and convenient cleansing. Different solubilizing agents for the potassium metaphosphate in this product may suitably be selected from many sodium salts like sodium bicarbonate, sodium citrate, sodium phosphate, sodium sulphate and mixtures thereof. In addition other suitable toilet cleaning ingredients such as, for example, sodium acid sulphate, $4(Na_3PO_4 \cdot 11H_2O)$ NaOCl chlorinated trisodium phosphate and the like may be added to the dry form of toilet bowl cleaning products. Such products can be easily prepared as powders or in tablet form for convenience of use. An example of a toilet bowl cleaner tablet which will effervesce for ease of disintegration and dissolution in the bowl water is listed in Example 4.

EXAMPLE 4

Effervescent Toilet Bowl Cleaner

| Sodium Lauryl Sulfate | 18.5 |
| --- | --- |
| $(KPO_3)_n$ | 20.0 |
| $NaHCO_3$ | 30.0 |
| Citric Acid | 30.0 |
| Fragrance | 0.5 |
| Mineral Oil | 1.0 |
| Color | (as needed) |
| | 100.00 |

A 20 g tablet of the above composition will be added to the toilet bowl, thickening the water with the results previously described.

Another unique application of potassium metaphosphate and a solubilizing agent is in the preparation of solid dosage pharmaceutical products to be added to water, dispersed or dissolved and subsequently ingested or used as a rinse by the user.

The addition of Kurrol salt and solubilizing agent will instantly produce a thickened, syrup-like gel. Such preparations allow the addition of pharmaceutical ingredients in the dry form to water. This is a particularly desirble means for delivering pharmaceutical ingredients which are not compatible or stable in water-containing liquid dosage forms. A typical composition is given in Example 5.

EXAMPLE 5

Pharmaceutical Powder

| Ingredient | % by weight |
| --- | --- |
| $(KPO_3)_n$ | 10.0 |
| $NaHCO_3$ | 20.0 |
| Citric Acid | 20.0 |
| Acetylsalicylic Acid | 6.5 |
| Sugar | 43.5 |
| Flavor | (as desired) |
| Color | (as desired) |
| | 100.00 |

A five gram effervescent tablet or granular dosage is added to 50 ml. of water resulting in a syrup-liquid which is easy to ingest. Typical properties of the syrup-like liquid produced from the composition of Example 5 are shown in Table II.

TABLE II

| Composition of Liquid | | | | | | |
| --- | --- | --- | --- | --- | --- | --- |
| $(KPO_3)_n$ | Na HCO$_3$ | Citric Acid | Sugar | Water | Viscosity | Remarks |
| 1.0 | 2.0 | 2.0 | 4.55 | 90.45 | 30 | Syrup-like effervescent liquid. |
| — | — | — | 4.55 | 95.45 | 1 | Water-like liquid. |
| 1.0 | — | — | — | 99.00 | 1 | Water-like liquid. |
| — | 2.0 | 2.0 | — | 96.00 | 1 | Water-like effervescent liquid. |

Different solubilizing agents for the potassium metaphosphate may be selected for this application from many sodium salts like sodium bicarbonate, sodium citrate, sodium phosphate and mixtures thereof. In addition, a wide range of pharmaceutical ingredients like analgesics, antihistamines, expectorants, antitussives, antibiotics and many others may be incorporated in dry form into compositions in accordance with this invention.

The following are additional preparations that benefit from this type of water-thickening dry delivery form of the present invention.

EXAMPLE 6

Fluorinated Mouthwash/Rinse

| Ingredient | % by weight |
|---|---|
| $(KPO_3)_n$ | 20.0 |
| Na Citrate | 20.0 |
| NaF | 10.0 |
| Sugar | 60.0 |
| Flavor | (as desired) |
| Color | (as desired) |
| | 100.00 |

A five gram powder, granular or tablet dosage is added to 50 ml of water resulting in a syrup-like liquid which is easy to use as a mouthwash rinse. The gel-like liquid will leave a residue that clings to the teeth enamel allowing the topical fluoride to remain in contact with the tooth surface for a longer time.

EXAMPLE 7

Denture Cleanser

| Ingredient | % by weight |
|---|---|
| $(KPO_3)_n$ | 20.0 |
| $NaHCO_3$ | 30.0 |
| Citric Acid | 30.0 |
| Sodium Lauryl Sulfate | 20.0 |
| Color/Flavor | (as desired) |
| | 100.00 |

A three gram tablet is added to 50 ml of water. Denture is placed in container and the gel-like liquid will foam and cling to the denture surfaces. After a period f time dentures are removed and rinsed.

EXAMPLE 8

Analgesic Soak

| Ingredient | % by weight |
|---|---|
| $(KPO_3)_n$ | 22.6 |
| $NaHCO_3$ | 37.5 |
| Citric Acid | 36.0 |
| Menthol | 1.0 |
| Mineral Oil | 2.0 |
| PEG-8 Dilaurate | 0.2 |
| Fragrance | 0.5 |
| Fumed Silica | 0.2 |
| Color | (as desired) |
| | 100.00 |

A twenty gram tablet is added to 50 liters of warm water. The gel-like fluid provides a vehicle with the analgesic ingredient (menthol).

Another unique application of potassium metaphosphate is in soap bars, synthetic detergent bars and creamy bases used for cleansing. In this case the solubilizing agent is the sodium salt of the detergent or fatty acid base used in the preparation of the bar or cream base. When a small amount of Kurrol salt is mixed in the cleansing base, the resulting product gives a much richer lather and a skin after-feel that is perceived by the user as leaving the skin soft and smooth.

The following are examples of this aspect of the invention.

EXAMPLE 9

Creamy Smooth—Synthetic Detergent Bar

| Ingredient | % by weight |
|---|---|
| $(KPO_3)_n$ | 2.0 |
| Soap Base: | |
| 80% Na Cocoate | 75.9 |
| 20% Na Tallowate | 17.1 |
| Water | 5.0 |
| | 100.00 |

EXAMPLE 10

Creamy Smooth—Synthetic Detergent Bar

| Ingredient | % by weight |
|---|---|
| $(KPO_3)_n$ | 2.0 |
| Sod. Cocoyl Isethionate | 98.0 |
| | 100.00 |

EXAMPLE 11

Anhydrous Cleanser Base

| Ingredient | % by weight |
|---|---|
| $(KPO_3)_n$ | 2.0 |
| Petrolatum | 30.0 |
| Mineral Oil | 11.0 |
| Sodium Cocoyl Isethionate | 27.0 |
| Sodium Lauryl Sulphate | 5.0 |
| Titanium Dioxide | 0.5 |
| Sugar | 24.0 |
| Fragrance | 0.5 |
| | 100.00 |

The resulting soap bars will produce a creamy smooth lather when wet. This rich cream-like perception is caused by a dramatic increase in the viscosity of the aqueous media as soap or detergent is dissolved in the presence of potassium polymetaphosphate. The sodium salt of the soap or appropriate synthetic detergent enhances the dissolution of the potassium Kurrol salt in the base giving a very high viscosity to the liquid media. This effect is summarized in Table III.

TABLE III

| Composition | | | Viscosity |
|---|---|---|---|
| $(KPO_3)_n$ | Soap Base**** | Water | (Centipose, 20° C.) |
| 0.5 | 0.5 | 99.0 | 1800 |
| 0.0 | 0.5 | 99.5 | 2 |
| 0.5 | 0.0 | 99.5 | 2 |
| | Sodium Cocoyl Isethionate | | |
| 0.5 | 0.5 | 99.0 | 680 |
| 0.5 | — | 99.5 | 2 |
| 0.0 | 0.5 | 99.5 | 2 |

****80% Na Cocoate; 20% Na Tallowate.

The high viscosity effect is temporary. After a period of time (3 to 120 minutes), as the potassium polymetaphosphate undergoes hydrolysis, there is a sharp viscosity drop in the solutions of Table III.

A similar effect can be obtained by adding the potassium polymetaphosphate to the anhydrous cleansing base of Example 11. The same sharp increase in viscosity (700 cps.) is obtained, giving a creamy and smooth lather.

The mineral oil and petroleum of Example 11 can be replaced with vegetable oils and shortenings with similar cosmetic effect.

Another unique application of potassium metaphosphate is in the formulation of deodorants and body powders. The potassium metaphosphate is blended with the solubilizing agent and properly dispersed in the deodorant and body powder media. The resulting products when placed in contact with body surfaces will have the property of holding and gelling perspiration or sweat, and keeping the user comfortably dry.

The following are examples of this aspect of the invention:

EXAMPLE 12

Body Powder

| Ingredient | % by weight |
|---|---|
| Corn Starch | 70.0 |
| $(KPO_3)_n$ | 15.0 |
| Na bicarbonate | 15.0 |
| | 100.00 |

EXAMPLE 13

Deodorant (Water Absorbant)

| Ingredient | % by weight |
|---|---|
| Dry Flo Corn Starch | 15.0 |
| Silicone Oil | 55.0 |
| $(KPO_3)_n$ | 15.0 |
| Na bicarbonate | 15.0 |
| | 100.0 |

The ability of the deodorant and body powder products to retain and gel fluids may be demonstrated by the following rather simple experiment.

Four grams of product is applied to common laboratory filter paper (6" diameter, coarse to medium grade, flow rate for water 10 ml per minute). The filter paper treated with product is placed in a suitable glass funnel and 20 ml of water is added to the funnel. The flow rate is determined by timing the amount of fluid eluded in 5 minutes. The results of the experiment are summarized in Table IV.

TABLE IV

| Composition | | | | | | |
|---|---|---|---|---|---|---|
| $(KPO_3)_n$ | $NaHCO_3$ | Starch | Silicone Oil | Crosslinked Polyacrylate | Flow Rate 20° | |
| 15 | 15 | 15 | 55 | — | 0.4 ml/min. | A |
| 15 | 15 | 15 | 54 | 1 | 0.2 ml/min. | B |
| — | 15 | 15 | 70 | — | 1.4 ml/min. | C |
| — | 15 | 15 | 69 | 1 | 0.8 ml/min. | D |

The results in Table IV show that the compositions containing potassium metaphosphate immediately gel the fluid and prevent the free flow of water through the filter paper. For the purpose of illustrating the water absorbent effect, some of the compositions were prepared with crosslinked polyacrylate polymer (super absorbent Nalco 1180, from Nalco Chemical Company), a polymer commonly used as a moisture absorbing additive in diapers and other products. This polymer was used as a positive control for absorbency. Even in composition D, which contains the crosslinked polyacrylate polymer, the flow rate is much faster than in materials prepared with the potassium Kurrol salt, that is, compositions A and B. The negative control, composition C, had the fastest flow rate, approximately 4 to 7 times faster than the filters treated with compositions A and B.

Similar effects can be obtained by adding the potassium polymetaphosphate to other suitable bases that can gel sweat and perspiration.

The compositions of the present invention are preferably packaged in substantially moisture-impervious packages.

While preferred examples of the invention have been set out in the body of the disclosure, it should be understood that the invention is not limited to those examples and can be practiced in many products of similar compositions.

What is claimed is:

1. A composition useful as a pharmaceutical, personal care or household product comprising a mixture of:
    i) potassium Kurroll's salt,
    ii) a solubilizing agent, and
    iii) at least one functional ingredient,
said mixture being substantially free of water.

2. A composition according to claim 1 wherein the amount by weight of said solubilizing agent present in the composition is at least equal to the amount by weight of said potassium polymetaphosphate.

3. A composition according to claim 1 wherein the amount by weight of said solubilizing agent present in the composition is at least twice the amount by weight of said potassium polymetaphosphate.

4. A composition according t claim 1 wherein said solubilizing agent is selected from the group consisting of the salt forms of soaps, detergents, surfactants and fatty acids.

5. A method of making a household, personal care or pharmaceutical product comprising:
    providing a mixture of potassium Kurroll's salt, a solubilizing agent and a functional ingredient, said mixture being substantially free from water; and
    dissolving the mixture in water, thereby producing a fluid having a viscosity greater than 1 centipoise at 20° C.

6. A method of making a household, personal care or pharmaceutical product composition comprising:
    providing a mixture of potassium Kurroll's salt, a solubilizing agent and a functional ingredient, and removing water from said mixture so that the product is substantially free from water.

7. A method according to claim 6 further comprising the step of forming said mixture into a solid form.

8. A method according to claim 6 wherein said solubilizing agent is selected from the group consisting of the salt forms of soaps, detergents, surfactants and fatty acids.

9. A composition as in claim 1 wherein said polymeric metaphosphate is present in an amount from about 0.5 to about 30 percent based on the weight of the composition.

10. A composition as in claim 1 further comprising an effervescing agent.

11. A composition as in claim 1 further comprising sodium bicarbonate, whereby the composition is rendered effervescent.

12. A method as in claim 1 wherein the mixture further comprises an effervescing agent.

* * * * *